United States Patent [19]

Segalowitz

[11] Patent Number: 5,234,450

[45] Date of Patent: * Aug. 10, 1993

[54] VALVULOTOME CATHETER

[76] Inventor: Jacob Segalowitz, 279 S. Beverly Dr., #1036, Beverly Hills, Calif. 90212

[*] Notice: The portion of the term of this patent subsequent to Mar. 3, 2009 has been disclaimed.

[21] Appl. No.: 753,781

[22] Filed: Sep. 3, 1991

Related U.S. Application Data

[62] Division of Ser. No. 386,215, Jul. 28, 1989, Pat. No. 5,092,872.

[51] Int. Cl.$^5$ .............................................. A61B 17/32
[52] U.S. Cl. ..................................... 606/159; 604/22; 606/170
[58] Field of Search ............... 606/159, 170, 166, 179, 606/156, 160, 167, 180; 30/162, 335, 304, 305; 604/22, 274; 227/19, DIG. 1; 128/4–6, 751

[56] References Cited

U.S. PATENT DOCUMENTS 4,427,014  1/1984  Bel et al. .......................... 128/757
4,926,858  5/1990  Gifford et al. ..................... 606/159

Primary Examiner—C. Fred Rosenbaum
Assistant Examiner—William Lewis
Attorney, Agent, or Firm—Flehr, Hohbach, Test, Albritton & Herbert

[57] ABSTRACT

A catheter-cutter for aorto-coronary bypass graft cutting of vein valves within a vein graft and for the in-situ bypass vein graft cutting of the valves within a vein includes at-least-one arcuate, razor-sharp, angled-tip cutting blade extending from the open distal end of the catheter, such at-least-one cutting blade being fixed or selectively extendable from the distal end of the catheter by optional control means carried at the proximal port of the catheter, the at-least-one cutting blade being effective to cleanly excise and clearly cut a valve, not merely rendering it relatively incompetent as present valvulotomes do. The catheter according to this invention may carry a fiberoptic viewer for observing the cutting process. A selectively inflatable balloon member may be provided about the catheter tube at its very distal end to accurately fix the position of the at-least-one cutting blade and, also, to act as a buffer, if desired, during catheter insertion and manipulation while being negotiated in a forward direction within the vein being modified.

10 Claims, 2 Drawing Sheets

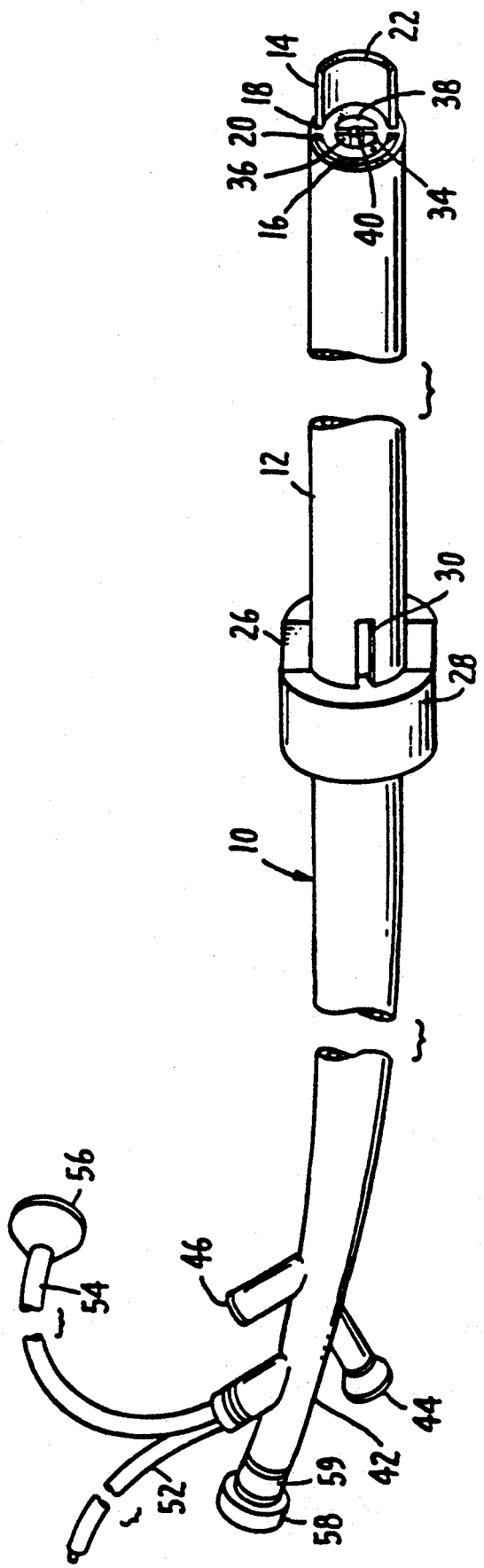

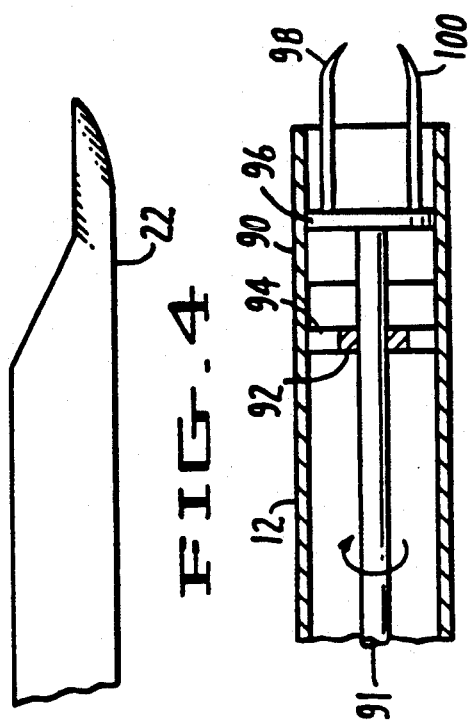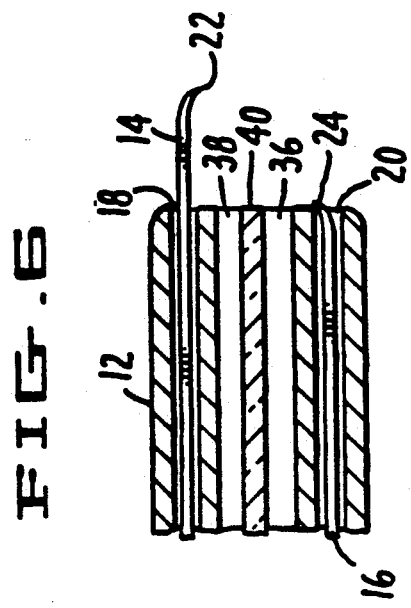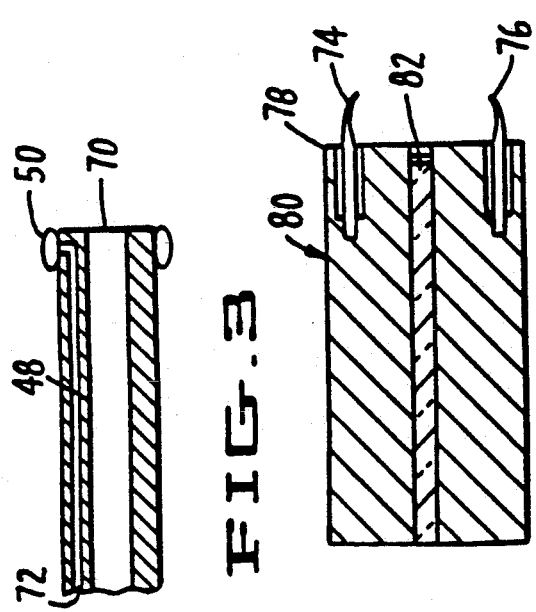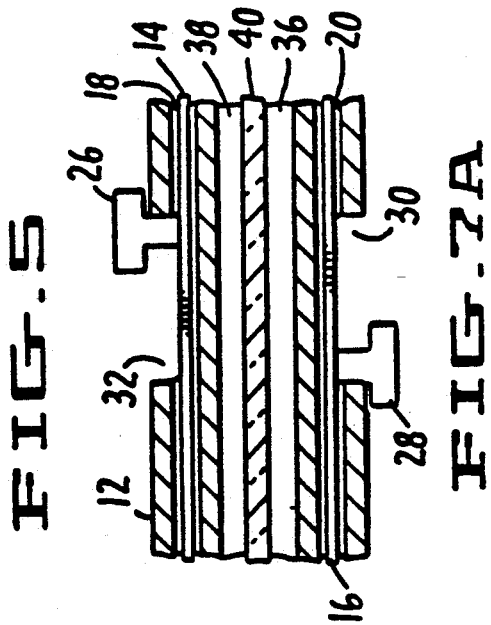

VALVULOTOME CATHETER

This is a division of application Ser. No. 07/386,215 filed Jul. 28, 1989, now U.S. Pat. No. 5,092,872.

BACKGROUND OF THE INVENTION

1. Field of the Invention

This invention relates to medical instrumentation and, more specifically, to such instrumentation applied in the field of cardiac surgery and peripheral vascular surgery.

2. Prior Art

Arterial reconstruction utilizing an autologous saphenous vein is widely used in the field of peripheral vascular surgery in the lower extremities and so has become well established as the customary graft source for aorto-coronary bypass graft surgery.

In peripheral vascular surgery in-situ bypass grafting has become more and more the operation of choice for bypassing the infrageniculate arteries and re-establishing arterial blood flow. The autogenous saphenous vein is historically similar to an artery and is the standard to which all other grafts are compared.

The earliest experiences with venous autogenous grafts, although experimental at that time, were gained by Gluck in 1894, followed by Exner and Hopfner in 1903. In the United States, Julian, et al., Lord and Stone, Dale, et al., and Linton and Darling pioneered the wide use of an autologous vein in femoral-popliteal arterial reconstructive procedures. The concept of using the saphenous vein, in-situ, is attributed to Karl Hall, in 1959, who suggested that the saphenous vein bypass might improve if the vein were left in place and the valves were rendered incompetent. He was the first to successfully report the use of the in-situ procedure as an arterial bypass, in 1962.

Further, the technique of in-situ bypass grafting was augmented by Leather and Karmody who used valve strippers to disrupt the grafted vein valves.

With the increasing experience worldwide, it was apparent that the crux of the in-situ vein graft was the method of removal of the valvular obstructions to distal arterial flow.

To achieve the in-situ disruption of the valves, various techniques have been used:

1. Incision of the valves by miniature scissors inserted through a venotomy proximal to the respective valve site.

2. Thin incising vein-strippers passed through the vein in the distal to the proximal direction.

3. Bullet-shaped metal strippers introduced in antero-grade or retrograde directions, employing incising parts in different shapes.

4. Long, thin-shaped valvulotomes with curved, hook-like incising tips which incise the valve leaflets upon pulling the device back through the valve.

5. Double cylinder strippers having incising parts incising the valves when such parts are pulled in a reverse direction.

6. Thin incision fingers extending from the open distal end of a catheter that is being pulled from the proximal part of the vein towards its distal portion by a pulling instrument that has been secured to the catheter after being introduced through the distal part of the vein.

In cardiac surgery, autologous saphenous vein grafts have been widely used since 1967 in aorto-coronary bypass grafting procedures for symptomatic coronary artery disease (CAD) treatment.

Autogenous reversed saphenous vein grafting has become routine for aorto-coronary bypass surgery.

With this method the saphenous vein valves are left intact and the vein is reversed. The distal portion of the grafted vein (which becomes proximal in the graft) is usually larger in diameter than the replaced coronary artery, resulting in reduced blood flow velocity in the vein graft compared with that in the coronary artery. These grafts provide an early patency rate of 98%; a routine elective mortality rate of approximately 1%; and a myocardial infarction rate of approximately 3%. The patency rate of coronary vein grafts is approximately 85% by the end of the first year postoperatively and the attrition rate continues approximately 2% per year for the next 4–5 years. Progressive stenosis continues, and the patency rate of coronary vein grafts at 3 years postoperatively is approximately 70% and approximately 60% at 5 years postoperatively.

At 10 years postoperative, atherosclerosis becomes the major cause of coronary vein graft failure. The vein graft occlusion rate doubles between 5 and 10 years, postoperatively.

Performance of coronary reversed saphenous vein grafts relates, among other factors, to the intact valves, which are implicated in graft failure. Studies suggest that valves do not open fully during reversed blood flow and cause a decrease in the graft blood flow rate at specific obstruction-related points. The undisrupted valves, non-collapsed against the wall of the grafted vein, may cause them to collapsed against the wall of the, grafted vein, may cause them to stay in the main blood stream and become a site of turbulence to laminar flow and an origin for thrombus formation under the cusps. This is especially true with the decreased blood flow rate in large diameter vein grafts and with poor run-off.

Thrombosis may lead, in these cases, to myocardial infarction or, later, to increased stenosis and occlusion. laminar flow at the venous valves causes a reaction of the vein grafts similar to a spasm, suggesting tat the valves may be a predisposed to an increased stenosis rate and a rapid occlusion rate of the vein grafts.

Additional experience evidenced that when more than one valve site was present in the body of the saphenous vein graft, occlusion, thrombus formation or accelerated progressive atherosclerosis seemed to occur in anatomic correlation to these valves. Good flow velocity is essential to the patency and integrity of coronary vein bypass grafts, while flow disturbance and decreased blood flow velocity are important influencing factors affecting their integrity as well as short term and long term patency.

Bisection of vein valves significantly increases the blood flow rate through the vein grafts.

Prior art devices, while rendering the saphenous veins relatively incompetent, did not remove the valves, with the result that complications such as stenosis, occlusion and thrombus formation, as previously recited, occurred. In cardiac surgery the protocol of coronary reversed vein grafts is subject to review and reversion if improved instrumentation becomes available, and is proven to be effective to enhance potency rate and integrity.

Therefore, it is an object of this invention to provide a medical instrument that will overcome the general problems recited hereinbefore.

It is a further object of this invention to provide an easy to operate cutting catheter that will cut and remove, effectively, the valves in the saphenous veins used as grafts for bypass peripheral surgery and aortocoronary bypass surgery.

SUMMARY OF THE INVENTION

Apparatus is provided for cutting the bi-cuspid venous valves free from the wall of a vein to be used in bypass vein graft surgery. This end is achieved by a catheter-vein cutter which comprises a cathetor having one or two arcuate (convex) tip-angle-edged razor-sharp cutting blades, positioned at its distal end tip. The catheter has one or two channel lumens. In its center or in a laterally displaced position, is a separate, shielded fiberoptic channel to provide real-time imaging control of manipulation of the catheter, manipulation of its blades and inspection of the results obtained. The fiberoptic channel is fixed in its position, extends from the distal tip of the catheter through the catheter and connects to an eyepiece at its proximal end, which may be connected to a video camera and to a TV monitor. The fiberoptic channel is either positioned fixed within a catheter support wall which forms two centered lumens of the catheter, or is fixed in a lateral position in the side wall of the catheter in the case where the catheter has only one centered lumen.

The two arcuate cutting blades, separated one from the other, can be manipulated each independently, or both simultaneously—resulting in that case in an almost completely closed pattern of a circular cut-line. The two cutting blades move in their respective separated channels of related size and shape, situated proximate to the periphery of the catheter, thus reaching in circular dimension almost the actual outer diameter (O.D.) of the catheter itself, thereby creating a minimal "dead space" between the circular cutting blades and the outer surface of the catheter, thus creating a spaced safety margin between the cutting blades and the inner surface of the vein wall. Because of this special safety margin, while negotiating forward the distal tip of the catheter, with its fixed or extendable cutting blades inadvertent damage to the vein will not occur. Each of the two arcuate cutting blade elements is angled at its tip-edge towards the center of the catheter (inwards) providing a further safety margin to prevent damaging the intimal surface of the vein when negotiating forward the catheter and its extended blade elements.

The arcuate blade elements are movable forward and backwards, extendable out of the distal end of the catheter and may be pulled back into the catheter to line up with its distal end This mechanism is controlled by a two-part, two-color, split-ring control unit situated at the proximal part of the catheter and connected to the two arcuate cutting blade elements housed in their own separated channels, so that pushing either of the semi-circular elements of the control split-ring unit in the direction from the proximal part to the distal end will extend the respective arcuate cutting blade element from the distal end of the catheter. Reverse manipulation of the split-ring control unit will withdraw the blade elements into the catheter and align the edges of the arcuate cutting blade elements with the distal end of the catheter. Since the split-ring control unit is of two parts, each of the cutting blade elements can be manipulated independently or simultaneously.

The arcuate, razor-sharp tip-angled cutting blade elements can be fixed at the distal-end of the catheter, extending permanently from the distal-end of the catheter for a predetermined length In that case, the arcuate cutting blade elements may be contiguous (or continuance) to form a completely closed circular shape and may be considered to be one circular, razor-sharp, tip-angled cutting blade. The method of its use involves advancing the catheter-cutter with its fixed or selectively extendable blade or blades through the blood vessel being treated, from its proximal portion towards its distal end or, conversely, if inserted through the distal part of the vessel, from its distal portion to its proximal portion, in either case excising completely and effectively any valves or other obstructions within the vein graft.

A low-profile, inflatable/deflatable single segment or multi-segment balloon may be positioned at the distal tip of the catheter to serve two purposes. First, when inflated, partially it covers completely the distal tip of the catheter, thus providing a beveled soft-tipped leading edge for the catheter when being inserted into the vein, or when negotiated forward within the lumen of the vein, thus preventing accidental vein-wall damage during the insertion or manipulation process, even in a tortuous vessel configuration. This structure is referred to by me as a "balloon-tipped" catheter. In addition to the safety feature just described, when the catheter tip is precisely positioned, the catheter may be fixed in this position by fully inflating the balloon tip.

The catheter can be disposable for single use, and is made from flexible materials. (i.e. polyethylene). The cutting blade elements, fixed or movable, can be made from metal.

At the proximal end of the catheter is a port connector that is in connection with one of the center lumens (with the smaller one, in case of two unequal lumens) for irrigation of fluid that will be flushed through that specific central lumen out through the distal end tip of the catheter.

Through the other lumen, a forceps-like biopsy device may be introduced to permit additional intraluminal manipulations. In the case in which the catheter has only one central lumen, both of the aforementioned activities may occur simultaneously through that single wide lumen.

The distal part of the catheter may be constructed to permit rotation of the fixed cutting blades around the axis of the cutter at a low rotational velocity, controlled from a small hand-held battery operated drive-motor unit.

BRIEF DESCRIPTION OF THE DRAWINGS

This invention can best be understood by taking the description which follows in conjunction with the drawings herein, in which:

FIG. 1 is a mechanical schematic diagram of valvulotome catheter, according to my invention;

FIG. 1A is an enlarged view of a portion of the catheter of FIG. 1;

FIGS. 2A, 2B and 2C are mechanical schematic diagrams showing alternative positioning of elements of my invention;

FIG. 3 is a partially cross-sectioned view of an alternative form of my invention;

FIG. 4 is a profile view of a cutting element for use in my invention;

FIG. 5 is a partially cross-sectioned view of an alternative form of my invention;

FIG. 6 is a partially cross-sectioned view of another embodiment of my invention; and, FIGS. 7A and 7B are partially cross-sectioned views of related portions of the device of FIG. 1.

DETAILED DESCRIPTION OF THE PREFERRED EMBODIMENTS

In FIG. 1 and 1A, valvulotome catheter 10 includes tube 12 having an outer diameter of from 1.5 mm. to 6.5 mm., the outer diameter being chosen to fit the blood vessel in which the instrument is to be used.

Tube 12 carries a pair of arcuate, razor-sharp cutting blade elements 14, 16 in channels 18, 20 located in the walls of tube 12. This can be seen more clearly in FIGS. 7A and 7B. Blade elements 14, 16 terminate at their distal ends in razor-sharp cutting edges 22, 24, respectively.

Blade elements 14, 16 are withdrawable into and extendable from channels 18, 20, respectively and independently, by way of ring-segment control elements 26, 28, respectively, which slide in slots 30, 32, respectively.

Central support element 34, as shown in FIG. 1, divides the inner space of tube 12 into two symmetrically disposed lumens 36, 38 which extend through tube 12. Support element 34 supports an optional fiberoptic bundle 40 which permits viewing the operation and effectiveness of cutting surfaces 22, 24 on blade elements 14, 16, respectively.

The proximal portion 42 of tube 12 includes flushing port connector 44 which communicates hydraulically with one of the lumens 36, 38 to permit flushing valve debris from the area being cut by cutting edges 22, 24.

A connector 46, pneumatically coupled to an air passage 48 (FIG. 3) in the wall of tube 12, is provided for inflating a buffer balloon 50 (FIG. 3).

A fiberoptic element 52 is adapted for the application of light thereto to illuminate the area where the excising of valves is occurring. The cutting scene may be observed optically or recorded for later study by way of fiberoptic element 54 and eyepiece 56.

Port connector 58 has a hemostatic valve 60 associated therewith It is coupled to one of the lumens 36, 38 for the introduction of biopsy-forceps-like catheters which may be required to extract excised valves or debris in the associated blood vessel.

Flushing port connector 44 is hydraulically coupled to the lumen not coupled to hemostatic valve port connector 58, for the introduction of irrigation fluid which may be necessary to flush excised valves and debris from the distal end of catheter 10 so as to assure a clear field of view when the fiberoptic channel 40 is being used.

Turning to FIGS. 2A, 2B and 2C, the positioning of support element 34 of tube 12 may vary.

In FIG. 2A, support element 34 is centrally disposed, thus making fiberoptic bundle 40 coaxial with tube 12 and producing two symmetrically disposed and equal-sized lumens 36, 38. In FIG. 2B, the support element 34 is displaced, the positioning of fiberoptic bundle 40 is also displaced from the center of tube 12 and two unequal lumens 60 and 62 are formed.

In FIG. 2C there is a single lumen 64 and fiberoptic 40 bundle is off-axis in the wall of tube 12.

In the embodiment of FIG. 2C, the same procedure of manipulating biopsy-forceps-like catheters and irrigating and flushing procedures will occur through the single lumen. In this configuration flushing port connector 46 and hemostatic port connector 58 are coupled to the common lumen 64.

Turning to FIG. 3, at the distal end 70 of catheter 10 a low-profile balloon 50 is affixed. One purpose of balloon 50 is to hold fixed the position chosen by the surgeon for end 70. Another is to provide safety to the side walls of the vessel when catheter manipulation is occurring. Balloon 50 is inflated, by gas or liquid, through channel 72 which is carried in the wall of catheter 10 from the proximal port to the distal end of catheter 10. Balloon 50 may be segmented in which case multiple inflation channels must be provided, one for each segment. A multi-position control valve is provided at the proximal port of catheter 10 to selectively control whether either or both segments of balloon 50 are inflated.

The selectable mode of inflation of balloon 50 permits a high degree of precision in the manipulation of catheter 10 and more accurate positioning thereof and of its cutting blades 22, 24.

FIG. 4 shows the profile of one of the razor-sharp, tip-angled cutting blades in catheter 12. Of course, angled-tip blades 22, 24 are highly polished and smooth on their external angled surfaces and sharpened to a razor-like edge.

In FIG. 5, angled-tip cutting blades 74 and 76 are shown fixed, longitudinally, in the distal end 78 of tube 80. Valve cutting is achieved by manipulating tube 80 from the proximal to the distal end of tube 80. Conversely, tube 80 may be moved from the distal to the proximal end of tube 12. In either mode, angle-tipped cutting blades 74, 76 sever any valves from the inner wall of the vein.

A fiberoptic bundle or channel 82 may be provided coaxially within tube 80.

In FIG. 6, the end portion 90 is rotatably supported from tube 12 by way of shaft 91 positioned by locating bearing 92 and support member 94. Shaft 91 terminates at its distal end in blade support member 96 which carries angled-tip, longitudinally-fixed cutting blades 98, 100. Rotation of shaft 91 at speeds of up to 50 r.p.m. by a small hand-held, battery operated drive motor at the proximal end of shaft 91 greatly enhances the cutting effectiveness of the catheter incorporating this feature.

While particular embodiments have been shown and described, it will be apparent to those skilled in the art that variations and modifications may be made therein without departing from the true spirit and scope of my invention. It is the purpose of the appended claims to cover all such variations and modifications.

I claim:

1. A valvulotome flexible elongate catheter including:
    an outer cylindrical wall;
    an inner cylindrical wall, means supporting said cylindrical inner wall in said cylindrical outer wall so that the inner wall is cylindrically spaced from said outer cylindrical wall to form at-least-one arcuate blade element chamber between said inner and outer walls;
    at-least-one blade element supported in said at-least-one blade element chamber and having a body portion and a cutting tip portion;
    said body portion being arcuate in transverse cross section;

said cutting tip portion being directed inwardly toward the longitudinal axis and terminating in a razor-sharp cutting edge; and means for fixing said at-least-one arcuate blade element in a fixed longitudinal position in said catheter and in a fixed radial position in said catheter.

2. A valvulotome flexible elongate catheter including:

an outer cylindrical wall;

an inner cylindrical wall, means supporting said cylindrical inner wall in said cylindrical outer wall so that the inner wall is cylindrically spaced from said outer cylindrical wall to form at-least-one arcuate blade element chamber between said inner and outer walls;

at-least-one blade element supported in said at-least-one blade element chamber in a fixed position and having a body portion and a cutting tip portion;

said body portion being arcuate in transverse cross section;

said cutting tip portion being directed inwardly toward the longitudinal axis and terminating in a razor-sharp cutting edge, said chamber forming a single lumen.

3. A valvulotome catheter, including:

a tube having an outer wall having a distal end and a proximal portion;

a rotatable end portion supported at said distal end;

a pair of inwardly directed cutting blades mounted in a fixed position in said rotatable end portion, each blade having an inwardly directed razor-sharp terminating end, and each blade being fixedly supported in said rotatable end portion to rotate therewith;

a shaft extending from said rotatable end portion to said proximal portion of said catheter; and, rotating means mechanically coupled to said shaft at the proximal portion thereof to cause rotation thereof and of said rotatable end portion.

4. A valvulotome flexible elongate catheter including:

an outer cylindrical wall;

an inner cylindrical wall, means supporting said cylindrical inner wall in said cylindrical outer wall so that the inner wall is cylindrically spaced from said outer cylindrical wall to form at-least-one arcuate blade element chamber between said inner and outer walls;

at-least-one blade element supported in said at-least-one blade element chamber and having a body portion and a cutting tip portion;

said body portion being arcuate in transverse cross section;

said cutting tip portion being directed inwardly toward the longitudinal axis and terminating in an inwardly directed razor-sharp cutting edge; and said body portion being continuous to form a complete single circular cutting edge and being fixed in longitudinal position within said catheter.

5. A valvulotome catheter including:

a cylindrical flexible elongate tube having a longitudinal axis, a radial axis and an outer wall and an inner wall;

at least one blade and means attached to said cylindrical tube for supporting said blade in a position spaced inwardly toward the longitudinal axis away from the outer wall, said blade being arcuate in cross section and having a body portion and a cutting tip portion, said cutting tip portion being directed radially inwardly and terminating in a razor sharp cutting edge.

6. Apparatus according to claim 5 wherein said at-least-one arcuate blade is fixed longitudinally with respect to said outer wall.

7. In a catheter for removing valves in a vein, a flexible cylindrical elongate member having a longitudinal axis and having an outer cylindrical wall, said flexible cylindrical elongate member having proximal and distal extremities, said distal extremity having a free end, a blade which is arcuate in cross section, means attached to said flexible cylindrical elongate member for supporting said blade in said flexible cylindrical elongate member so that it is adapted to protrude from the free end and in a position spaced inwardly towards the longitudinal axis and away from the outer cylindrical wall, said blade having a forwardly extending cutting edge, said flexible cylindrical elongate member having sufficient rigidity so that the distal extremity can be advanced and rotated by advancement and rotation of the proximal extremity to cause the blade to excise said valves in said vein while said flexible cylindrical elongate member is disposed in said vein.

8. A catheter as in claim 7 wherein said flexible cylindrical elongate member has a lumen therein and wherein a fiber optic bundle is disposed in said lumen and extends to the distal extremity of the flexible cylindrical elongate member.

9. A catheter as in claim 7 together with a low profile inflatable balloon mounted on the outer wall of the distal extremity of the flexible cylindrical elongate member, said flexible cylindrical elongate member having a balloon inflation lumen therein in communication with the interior of the inflatable balloon, said balloon when inflated serving to ensure that the blade will not come into contact with the vein.

10. A catheter as in claim 7 together with means mounted on the flexible cylindrical elongate member for moving said blade between extended and retracted positions.

* * * * *